US00PP22316P2

(12) United States Plant Patent
Radler

(10) Patent No.: US PP22,316 P2
(45) Date of Patent: Dec. 13, 2011

(54) CLIMBING ROSE PLANT NAMED 'RADFIFTH'

(50) Latin Name: *Rosa hybrida*
Varietal Denomination: cv. Radfifth

(75) Inventor: William J. Radler, Greenfield, WI (US)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 12/801,147

(22) Filed: May 25, 2010

(51) Int. Cl.
*A01H 5/00* (2006.01)

(52) U.S. Cl. ..... Plt./113; Plt./109

(58) Field of Classification Search ..... Plt./113, Plt./114, 112, 106, 107, 105, 109, 102
See application file for complete search history.

*Primary Examiner* — Kent L Bell

(74) *Attorney, Agent, or Firm* — Buchanan Ingersoll & Rooney PC

(57) ABSTRACT

A new and distinct variety of rose plant is provided which forms in abundance on a substantially continuous basis attractive single to semi-double blossoms that are coral in coloration with substantial irregular cream-to-yellow striping. The vegetation is vigorous and the growth habit is upright and climbing. Attractive ornamental medium green foliage having a satiny finish is displayed. During observations to date the disease resistance has been good, particularly with respect to blackspot. The cold hardiness of the new variety also is excellent, particularly for a climbing rose. The new variety is well suited for growing as distinctive ornamentation in parks, gardens, and residential settings. Instead of a climber, the plant can alternatively be trimmed and grown as a compact rose bush in the absence of support.

1 Drawing Sheet

Botanical/commercial classification: *Rosa hybrida*/Climbing Rose Plant.

Varietal denomination: cv. Radfifth.

SUMMARY OF THE INVENTION

The new variety of *Rosa hybrida* rose plant of the present invention was created at Greenfield, Wis., U.S.A., by artificial pollination wherein two parents were crossed which previously had been studied in the hope that they would contribute the desired characteristics. The cross was carried out during June 1999. The female parent (i.e., the seed parent) was the 'Meioffic' variety (U.S. Plant Pat. No. 9,998). The male parent (i.e., the pollen parent) of the new variety was the 'Wekroalt' variety (U.S. Plant Pat. No. 11,518). The 'Meioffic' variety is being marketed under the JOHANN STRAUSS trademark, and the 'Wekroalt' variety is being marketed under the FOURTH OF JULY trademark. The parentage of the new variety can be summarized as follows:

'Meioffic'×'Wekroalt'.

The seeds resulting from the above pollination were sown and small plants were obtained which were physically and biologically different from each other. Selective study resulted in the identification of a single plant of the new variety.

It was found that the new climbing rose plant of the present invention possesses the following combination of characteristics:

(a) abundantly and substantially continuously forms attractive single or semi-double blossoms that are coral in coloration with substantial irregular cream-to-yellow striping,
(b) exhibits an upright and climbing growth habit,
(c) forms vigorous vegetation, (d) forms attractive ornamental satiny medium green foliage,
(e) exhibits good resistance to blackspot, and
(f) exhibits excellent cold hardiness for a climbing rose.

The new variety displays a good repeat blooming character. The winter hardiness is noteworthy for a climbing rose plant. The growth habit is very vigorous and the canes are medium in caliper for the class.

The new variety well meets the needs of the horticultural industry. It can be grown to advantage as an attractive climber in parks, gardens, public areas, and in residential settings. It alternatively can be trimmed and grown as a compact rose bush in the absence of support. The new variety is particularly well suited for providing attractive ornamentation wherever it is grown. The blossom coloration contrasts nicely with the satiny medium green foliage.

The new variety of the present invention can be readily distinguished from its ancestors, as well as other climbing rose varieties. More specifically, the 'Meioffic' variety parent is a Floribunda rose which exhibits Orient Pink blossoms suffused with Aureolin Yellow on the upper surface and Dawn Pink suffused with Aureolin Yellow on the under surface, and the 'Wekroalt' variety parent exhibits red blossoms striped with white. Also, the new variety of the present invention can be readily distinguished from the 'Radbrite' variety (U.S. Plant Pat. No. 17,391) and the 'Radmor' variety (U.S. Plant Pat. No. 19,433). The blossoms of the 'Radbrite' variety are pink with a yellow eye, and the blossoms of the 'Radmor' variety are soft pink and finish to shell pink in coloration.

The characteristics of the new variety have been found at Wasco, Calif., U.S.A., and near West Grove, Pa., U.S.A., to be homogeneous and stable and to be strictly transmissible by asexual propagation, such as budding, grafting, and the rooting of cuttings, from one generation to another. The new variety reproduces in a true-to-type manner by such asexual propagation.

The new variety has been named 'Radfifth' and is being marketed under the CITRUS BURST trademark.

BRIEF DESCRIPTION OF THE PHOTOGRAPH

The accompanying photograph shows from above, as nearly true as it is reasonably possible to make the same in a color illustration of this character, a typical flowering plant of the new variety. The illustrated rose plant was approximately two years of age and is depicted during the month of June while growing near West Grove, Pa., U.S.A. The attractive multi-colored blossoms in various stages of development and satiny green foliage are shown.

DETAILED DESCRIPTION

The chart used in the identification of colors is that of The Royal Horticultural Society (R.H.S. Colour Chart), London, England. The description is based on the observation of two-year-old specimens of the new variety during May while growing outdoors in containers near West Grove, Pa., U.S.A. Class: Climbing Rose.

Plant:

*Height.*—Approximately 3 to 4 feet on average at the end of the growing season, and commonly assumes a mature height of approximately 8 feet.

*Width.*—Approximately 3 to 4 feet on average at the end of the growing season, and commonly continues to display approximately the same width at full maturity.

*Habit.*—Upright and climbing.

Branches:

*Color.*—Young stems: commonly Yellow-Green Group 144A. adult wood: near Yellow-Green Group 148A.

*Texture.*—Young stems: Smooth. adult wood: somewhat coarse to the touch.

*Cane length.*—Typically approximately 45 cm on average for a two-year-old plant.

*Cane diameter.*—Typically approximately 7 to 10 mm on average for a two-year-old plant.

*Thorns.*—On young wood: commonly several large nearly straight thorns are present having a coloration of Green-Yellow Group 1C and a length of approximately 8 mm on average with a moderately long base that is approximately 5 mm in length and approximately 1 mm in width on average. on mature wood: commonly the thorns assume a coloration of Greyed-Orange Group 117B.

Leaves:

*Leaflet number.*—3, 5, and 7.

*Leaflet texture.*—On the upper side generally smooth with an indentation towards the mid-vein, and on the under side smooth commonly with some prickles along the midrib.

*Leaf size.*—Commonly approximately 10 to 12 cm in length on average, and approximately 8 to 10 cm in width on average at the widest point.

*Leaflet shape.*—Generally oval to somewhat ovate with acute to somewhat acuminate apices, and rounded bases.

*Leaflet margins.*—Serrulate.

*Leaflet size.*—Commonly approximately 4 to 5 cm in length on average, and approximately 3 to 4 cm in width on average at the widest point.

*Overall appearance.*—Abundant, and medium green with a satiny finish.

*Color.*—Young leaves: upper surfaces commonly between Green Group 139A and Yellow-Green Group 147A, and under surfaces commonly between Green Group 139C and Yellow-Green Group 147C. mature leaves: upper surfaces commonly are between Green Group 139A and Yellow-Green Group 147A, and under surfaces commonly are near Yellow-Green Group 147B and 147C.

*Stipules.*—Approximately 10 mm in length on average, approximately 6 mm in width on average at the widest point, possess moderately narrow medium-to-long points that commonly turn at an angle of more than 45 degrees, and near Green Group 138A in coloration.

*Petiole.*—Commonly approximately 4 cm in length on average, approximately 3 mm in diameter on average, slightly bristly in texture, and near Green Group 138A in coloration.

*Rachis.*—Commonly approximately 6 cm in length on average, approximately 2 mm in diameter on average, the upper side is moderately grooved with some stipulate glands and hairs at the edges of the groove, and the underside is somewhat rough with a few stipulate glands and numerous small prickles.

Inflorescence:

*Bearing.*—Commonly in clusters of approximately 4 to 6 blossoms. The clusters commonly are irregularly rounded and commonly are borne on medium to long stems having lengths of approximately 30 to 40 cm.

*Peduncle.*—Very strong, usually erect, commonly approximately 8 mm in diameter, commonly bear stipulate glands and hairs, and commonly near Yellow-Green Group 144A and 144B in coloration.

*Sepals.*—Length: commonly approximately 2 cm on average. width: commonly approximately 8 mm on average. margins: commonly with extensions and lined with a few stipulate glands and hairs. texture: the inner surface commonly is lined with very fine wooly tomentum. apex: acute. color: commonly Yellow-Green Group 144A fading to Yellow-Green Group 144C on the upper surface, and Green Group 143C on the under surface. number: five.

*Buds.*—Shape: generally pointed to urn-shaped as the calyx breaks. size: small to medium. length: as the calyx breaks commonly approximately 2 cm on average. diameter: as the calyx breaks commonly approximately 1 to 1.5 cm on average at the widest point. color (as the calyx breaks): commonly Yellow Group 12C with some striations of Red Group 50A.

*Flower.*—Form: single to semi-double. configuration: when partially opened very low-centered with the petals being somewhat loosely spiraled and the petal edges being somewhat slightly reflexed outwards, and when fully opened somewhat flattened with the petal edges being generally flat to undulated and very slightly reflexed outward. diameter: commonly approximately 8 cm on average when fully open. color (when blooming) coral petals are prominently marked in varying patterns of cream and yellow stripes and spots. upper surface: commonly towards the apex Red Group 43B, and commonly towards the area of attachment Yellow Group 6B with some petals bearing Yellow-White Group 158B. under surface: commonly towards the apex a blend of Red Group 49A and Red Group 51A, and towards the area of attachment Yellow Group 8A and Yellow Group 11B.

lastingness: commonly approximately 1 or 2 days or more on the plant depending upon environmental conditions, and approximately 1 day when cut and placed in a vase. petal number: commonly approximately 8 to 12 on average. petal size: commonly approximately 3 cm in length on average and approximately 3 cm in width on average. petal texture: medium to thick in substance, the upper surfaces are moderately velvety to slightly satiny, and the under surfaces are mostly satiny to somewhat shiny. petaloid number: commonly approximately 1 or 2 on average, and irregularly arranged per flower. petaloid size: commonly approximately 1.5 cm in length and approximately 1.1 cm in width. petaloid color: near Yellow Group 3C on the upper surface, and near Yellow Group 3D on the under surface. petal shape: nearly round to very broadly obovate, commonly with an obcordate tip and a cuneate base. fragrance: very light and mildly sweet. petal drop: very good, with the petals commonly dropping cleanly and freely. The pistils and stamen often persist (e.g., a day longer). stamen number: commonly approximately 90 to 100 on average, and regularly arranged around the pistils.

*Anthers.*—Commonly approximately 1 to 2 mm in diameter, when immature commonly between Yellow Group 13C and Yellow-Orange Group 20A in coloration, and when mature between Greyed-Orange Group 163A and Greyed-Orange Group 165A in coloration.

*Filaments.*—Commonly approximately 7 to 12 mm in length on average, most bear anthers, and Yellow Group 13A commonly suffused with Red Group 41A in coloration.

*Pollen.*—Moderate to abundant in quantity, and near Yellow Group 13B in coloration. pistils: separate and free, and commonly approximately 30 to 40 in number on average.

*Stigmas.*—Yellow-Orange Group 19A in coloration.

*Styles.*—Moderately uneven in length, commonly approximately 3 to 5 mm in length on average, approximately 0.25 mm in diameter, and near Yellow Group 8D suffused with Red Group 46D in coloration.

*Receptacle.*—Substantially round in shape, commonly approximately 7 mm in diameter on average, commonly bears a somewhat bristly surface texture, near Yellow-Green Group 144B in coloration, and the ovaries commonly are enclosed in the calyx.

Development:

*Vegetation.*—Vigorous.

*Blossoming.*—Very abundant and substantially continuous during the growing season.

*Resistance to diseases.*—Good particularly with respect to blackspot when compared to commercial rose varieties being grown under comparable conditions near West Grove, Pa., U.S.A.

*Cold hardiness.*—Good when grown at Greenfield, Wis., U.S.A., and near West Grove, Pa., U.S.A.

*Propensity to form hips.*—No hips observed during observations to date.

The new 'Radfifth' variety has not been observed under all possible environmental conditions to date. Accordingly, it is possible that the phenotypic expression may vary somewhat with changes in light intensity and duration, cultural practices, and other environmental conditions.

I claim:

1. A new and distinct climbing rose plant characterized by the following combination of characteristics:

(a) abundantly and substantially continuously forms attractive single or semi-double blossoms that are coral in coloration with substantial irregular cream-to-yellow striping, (b) exhibits an upright and climbing growth habit, (c) forms vigorous vegetation, (d) forms attractive ornamental satiny medium green foliage, (e) exhibits good resistance to blackspot, and (f) exhibits excellent cold hardiness for a climbing rose; substantially as herein shown and described.

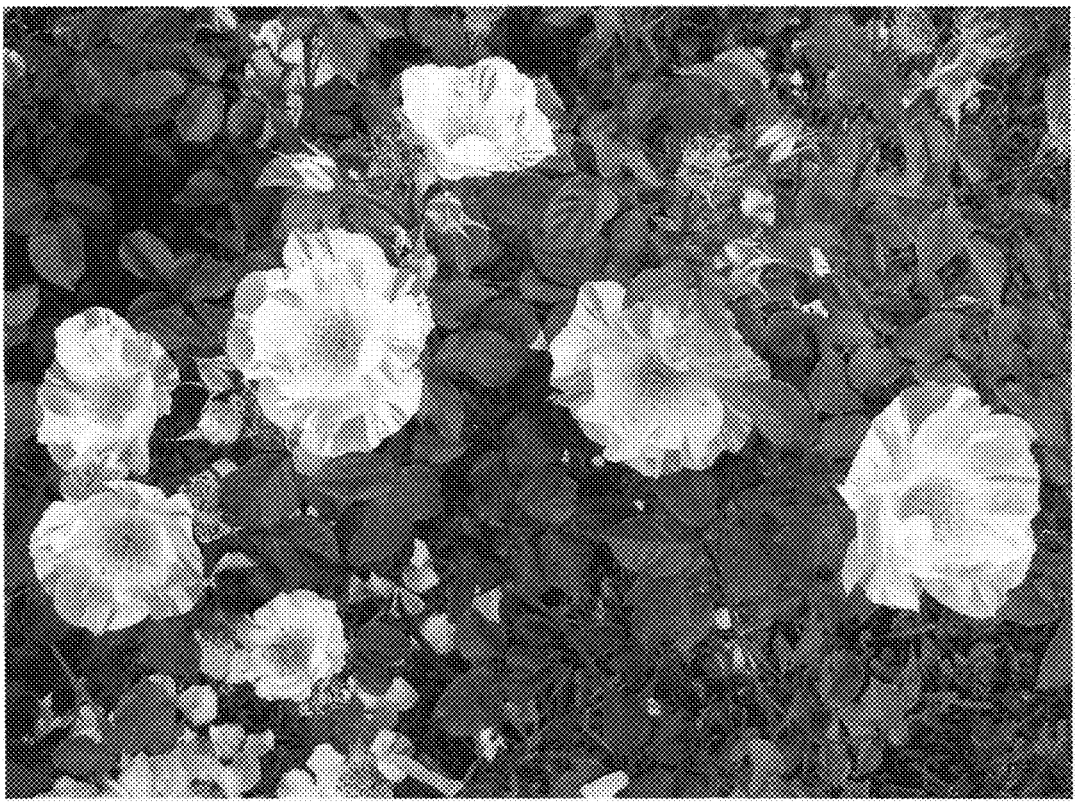

* * * * *